United States Patent
Thoreson et al.

(10) Patent No.: US 12,303,945 B2
(45) Date of Patent: May 20, 2025

(54) METHODS FOR CLEANING-IN-PLACE

(71) Applicant: Regenesis Bioremediation Products, San Clemente, CA (US)

(72) Inventors: Kristen A. Thoreson, San Clemente, CA (US); Paul R. Erickson, San Clemente, CA (US); Scott B. Wilson, San Clemente, CA (US)

(73) Assignee: REGENESIS BIOREMEDIATION PRODUCTS, San Clemente, CA (US)

( * ) Notice: Subject to any disclaimer, the term of this patent is extended or adjusted under 35 U.S.C. 154(b) by 0 days.

(21) Appl. No.: 17/498,250

(22) Filed: Oct. 11, 2021

(65) Prior Publication Data
US 2022/0111423 A1  Apr. 14, 2022

Related U.S. Application Data

(60) Provisional application No. 63/091,265, filed on Oct. 13, 2020.

(51) Int. Cl.
| | | |
|---|---|---|
| *B08B 3/08* | (2006.01) | |
| *A61L 2/18* | (2006.01) | |
| *B08B 3/10* | (2006.01) | |
| *C11D 17/00* | (2006.01) | |

(52) U.S. Cl.
CPC ........ *B08B 3/08* (2013.01); *A61L 2/18* (2013.01); *B08B 3/10* (2013.01); *C11D 17/0013* (2013.01); *A61L 2202/17* (2013.01)

(58) Field of Classification Search
None
See application file for complete search history.

(56) References Cited

U.S. PATENT DOCUMENTS

| | | | | |
|---|---|---|---|---|
| 5,460,792 | A  * | 10/1995 | Rosenbaum | A62D 3/38 |
| | | | | 423/245.3 |
| 6,326,340 | B1 * | 12/2001 | Labib | C11D 3/14 |
| | | | | 510/370 |
| 6,952,169 | B1 * | 10/2005 | Simtion | A62C 37/44 |
| | | | | 340/577 |
| 7,111,682 | B2 | 9/2006 | Blaisdell | |
| 7,387,723 | B2 | 6/2008 | Jordan | |
| 7,585,132 | B2 | 9/2009 | Imbrie | |
| 8,623,273 | B2 * | 1/2014 | Lu | F28F 19/00 |
| | | | | 252/387 |
| 8,802,049 | B2 | 8/2014 | Farone et al. | |
| 9,770,743 | B2 | 9/2017 | Mork et al. | |
| 9,776,898 | B2 | 10/2017 | Wilson et al. | |
| 10,005,684 | B2 | 6/2018 | Wilson et al. | |
| 10,478,876 | B2 | 11/2019 | Thoreson et al. | |
| 10,512,957 | B2 | 12/2019 | Thoreson et al. | |
| 2003/0121532 | A1 * | 7/2003 | Coughlin | B08B 9/057 |
| | | | | 134/22.12 |
| 2006/0006114 | A1 | 1/2006 | Deskins | |
| 2010/0036189 | A1 * | 2/2010 | Lee | B09C 1/02 |
| | | | | 588/316 |
| 2011/0036410 | A1 | 2/2011 | Tontegode | |
| 2011/0158872 | A1 * | 6/2011 | Ariya | B01D 53/885 |
| | | | | 977/773 |
| 2011/0254231 | A1 | 10/2011 | Isenberg et al. | |
| 2014/0290958 | A1 * | 10/2014 | Marr | C09K 8/524 |
| | | | | 166/311 |
| 2015/0034559 | A1 | 2/2015 | Mork et al. | |
| 2018/0327600 | A1 | 11/2018 | Thoreson et al. | |
| 2018/0327623 | A1 | 11/2018 | Thoreson et al. | |
| 2019/0201951 | A1 | 7/2019 | Thoreson et al. | |
| 2020/0038926 | A1 | 2/2020 | Freim, III et al. | |
| 2021/0060621 | A1 * | 3/2021 | Seippel | B08B 9/0328 |
| 2021/0170363 | A1 | 6/2021 | Thoreson et al. | |

FOREIGN PATENT DOCUMENTS

| | | | | | |
|---|---|---|---|---|---|
| WO | WO-2015097728 | A1 * | 7/2015 | ......... | H01F 17/0013 |
| WO | WO-2019113634 | A1 * | 6/2019 | ............. | A61B 1/125 |

OTHER PUBLICATIONS

Rodriquez, Kari; PCT Search Report and Written Opinion; Jan. 21, 2022; 8 pages; Alexandria, Virginia.

* cited by examiner

*Primary Examiner* — Michael E Barr
*Assistant Examiner* — Arlyn I Rivera-Cordero
(74) *Attorney, Agent, or Firm* — STETINA GARRED BRUCKER & NEWBOLES

(57) ABSTRACT

Methods of cleaning-in-place are contemplated whereby a suspension is introduced into a mechanical system containing contaminated surfaces. The solid-phase particles suspended within the suspension are functional to at least partially clean the contamination. Following the at least partial cleaning, the suspension may be purged from the mechanical system. In this way, it may be seen that modalities of decontamination may be achieved which may be operative to decontaminate many types and degrees of contamination.

20 Claims, No Drawings

METHODS FOR CLEANING-IN-PLACE

CROSS-REFERENCE TO RELATED APPLICATIONS

This application relates to and claims the benefit of U.S. Provisional Application No. 63/091,265 filed Oct. 13, 2020, and entitled "IMPROVED METHODS FOR CLEANING-IN-PLACE," the entire disclosure of which is hereby wholly incorporated by reference.

STATEMENT RE: FEDERALLY SPONSORED RESEARCH/DEVELOPMENT

Not Applicable

BACKGROUND

1. Technical Field

The present disclosure relates generally to the field of cleaning of contaminated surfaces. More particularly, the present disclosure relates to improved methods for cleaning contaminated surfaces within machinery or other equipment without requiring substantial transportation or disassembly of that equipment.

2. Related Art

Cleaning-in-place (CIP) is a method of cleaning equipment with minimal dismantling or operator involvement. Conventional CIP methods typically involve the process of flowing water through the equipment with laminar or turbulent flow at variable temperatures, and often include the use of chemicals or cleaning agents. Substances that are often targeted for removal in CIP systems include organic compounds, inorganic compounds, bacteria and/or viruses. The cleaning agents that can be used within a CIP process are typically limited to those that are soluble and/or entirely liquid phase due to the need to be able to flow them in and out of the system.

In other applications, solid-phase particles are widely used to remove or destroy a variety of substances within aqueous systems. For example, activated carbon is often employed to remove organic chemicals from contaminated groundwater through the process of adsorption, whereby the chemicals of concern bind to sorption sites throughout the carbon particle. The most common practice utilizing activated carbon is to pump the water to be treated through vessels holding granular activated carbon particles (generally greater than 300 microns in size) to filter the organic chemicals from the incoming water stream. Powdered activated carbon has also been used, albeit less frequently.

In other words, conventional systems for using activated carbon to decontaminate environments suffer from a deficiency that in that they are typically constrained by the requirement of bringing the contaminated water into the activated carbon-containing vessel. The same is true for many other systems for decontamination which use solid-phase particles. This limitation means that in the case of many solid reagents, such as sorbents, which may be advantageous for removing contaminants, the use of such reagents is not appropriate for systems or equipment that require cleaning-in-place.

It is therefore desirable to have improved methods for cleaning-in-place which utilize solid-phase particles that can be deployed in a CIP process, in which the solid-phase particles may be effectively transported through equipment to reach contaminated zones while remaining highly reactive/sorbent toward the target contaminants. The ability to use solid-phase particles can alleviate common deficiencies in CIP processes by improving the cleaning efficiency, lowering energy costs, minimizing water consumption, and decreasing total waste volumes.

BRIEF DESCRIPTION

To solve these and other problems, a method of cleaning-in-place is described herein whereby a suspension may be introduced into a mechanical system containing contaminated surfaces. The solid-phase particles suspended within the suspension may be configured to be functional to at least partially remove the contamination. Following the at least partial cleaning, the suspension may be purged from the mechanical system. In this way, it may be seen that modalities of decontamination may be achieved which may be operative to decontaminate many types and degrees of contamination for which it may not be feasible to decontaminate via conventional methods of decontamination.

According to various embodiments of the herein disclosed methods, a method of cleaning a contaminated surface within a mechanical system is contemplated, the method comprising the steps of introducing a suspension into a mechanical system having at least one contaminated surface such that the suspension comes into contact with the at least one contaminated surface, the suspension comprising a plurality of solid-phase particles, maintaining the suspension in contact with the at least one contaminated surface for a sufficient length of time to at least partially decontaminate the at least one contaminated surface, and purging the suspension from the mechanical system, wherein the plurality of solid-phase particles is at least partially operative to at least partially decontaminate the at least one contaminated surface.

According to certain more particular variations in the embodiments of the disclosed methods, it is contemplated that the solid-phase particles may be present within the suspension in an amount from 0.0001% to 70% by weight. It is further contemplated in other embodiments that in the suspension, the solid-phase particles may have a particle size distribution D90 value of less than 50 microns, or even less than 15 microns.

According to additional embodiments, it is contemplated that the step of maintaining the suspension in contact with the at least one contaminated surface may comprise continuous recirculation of the suspension through the mechanical system, flowing the suspension through the mechanical system in a single pass, allowing the suspension to remain within the mechanical system with zero flow, or combinations thereof.

It is also contemplated that in first embodiments of the contemplated methods, that the temperature or pressure of the suspension may be controlled. For example, during the step of maintaining the suspension in contact with the at least one contaminated surface, the suspension may be maintained at a predefined temperature, or may be varied. Likewise, during the step of maintaining the suspension in contact with the at least one contaminated surface, the suspension may be maintained at a predefined pressure, or may be varied.

According to still further variations of disclosed embodiments, the suspension may further comprise one or more reagents in addition to the plurality of solid-phase particles, the one or more reagents being further operative to at least partially decontaminate the contaminated surface.

It is further contemplated that following the step of purging the suspension from the mechanical system, a further cleaning process for at least partially decontaminating the at least one contaminated surface may be performed. Alternatively, or in addition to this, it is additionally contemplated that prior to the step of introducing a suspension into a mechanical system, a further cleaning process for at least partially decontaminating the at least one contaminated surface may be performed.

According to the presently contemplated methods, it is contemplated that the plurality of solid-phase particles may be selected from: activated carbon, zeolites, alumina, apatite, iron oxides, iron oxyhydroxides, silica, silicates, titanium oxides, or combinations thereof.

It is additionally contemplated that according to different variations of the presently disclosed methods, the at least one contaminated surface may comprise organic contaminants selected from: hydrocarbons, halogenated hydrocarbons, pesticides, herbicides, energetic materials, micropollutants, and combinations thereof. The at least one contaminated surface may also comprise a halogenated hydrocarbon selected from: per- and polyfluoroalkyl substances (PFAS), a chlorinated solvent, or combinations thereof. The at least one contaminated surface may additionally comprise inorganic contaminants selected from: heavy metals, anions, cations, and combinations thereof. The at least one contaminated surface may further comprise pathogenic contaminants selected from: bacteria, a virus, a protozoa, algae, fungi, viroids, prions, spores, and combinations thereof.

According to still additional variations of the herein disclosed methods, it is contemplated that the suspension may further comprise one or more additives selected from: sodium carboxymethyl cellulose, polyacrylic acid, sodium lignosulfonate, polydiallyldimethylammonium chloride, alkyl carboxylates, alkyl and aryl sulfates, alkyl polyethylene oxides, ethylene oxides, and combinations thereof. It is further contemplated that the suspension may further comprises one or more amendments selected from: a biocide, a bleaching agent, chlorine, chloramine, a polyelectrolyte, a chelating agent, a buffering agent, a rheology modifier, a thickening agent, a thinning agent, a polymer, an oxidizing agent, a reducing agent, a surfactant, a bacterium, and combinations thereof.

According to still further embodiments of the herein disclosed methods, the mechanical system may comprise: a machinery, a pipework, a vessel, or combinations thereof.

DETAILED DESCRIPTION

According to the various examples discussed herein, methods of cleaning-in-place are contemplated wherein a suspension may be introduced into a mechanical system containing contaminated surfaces. The solid-phase particles suspended within the suspension may be functional to at least partially clean the contamination. Following the at least partial cleaning, the suspension may be purged from the mechanical system. In this way, it may be seen that modalities of decontamination may be achieved which may be operative to decontaminate many types and degrees of contamination for which it may not be feasible to decontaminate via conventional methods of decontamination.

Many mechanical systems may be seen to benefit from being cleaned using cleaning-in-place methodologies, whereby the mechanical system does not need to be substantially disassembled or transported to a specialized location. In the case of some mechanical systems, cleaning in place may even represent the more economically or practically feasible way of removing contaminants from within that system. Exemplary mechanical systems which may be treated via cleaning-in-place methodologies include, for example but without limitation, machineries, pipeworks, vessels, or combinations thereof.

A suspension is generally considered to be a heterogenous mixture in which insoluble particles of one substance, usually from 2 to 500 nm in diameter, are distributed throughout a second substance. For example, suspension which may be utilized within the presently disclosed methods include the suspensions disclosed in, among other references, published patent application US 2015/0034559 A1 by Mork et al. entitled COLLOIDAL AGENTS FOR AQUIFER REMEDIATION, the teachings of which are expressly incorporated herein by reference, U.S. Pat. No. 10,478,876 by Thoreson et al. entitled METHOD OF INCREASING HYDROPHOBICITY OF NATIVE WATER-BEARING ZONES, the teachings of which are expressly incorporated herein by reference, and published patent application US 2019/0201951 A1 by Thoreson et al. entitled METHODS FOR REMEDIATING CONTAMINATED SOIL AND GROUNDWATER USING SOLID-PHASE ORGANIC MATERIALS, the teachings of which are expressly incorporated herein by reference, and published patent application US 2020/0038926 A1 by Freim, III et al. entitled COMPOSITIONS AND METHODS FOR REMOVING CHLORINATED HYDROCARBONS, the teachings of which are expressly incorporated herein by reference.

It is herein contemplated that the particular identity of the solid-phase particles to be included within a suspension according to the presently disclosed methods may vary according to the particular nature and requirements of the mechanical system, the contaminated surface(s), and the contaminants. For example, according to an exemplary embodiment of the present disclosure, it is contemplated that the herein disclosed methods may be utilized in order to perform cleaning-in-place upon fire suppression systems in which aqueous film-forming foams (AFFF) have been used. Such systems have in the past been commonly used in aircraft hangers, refineries, on seagoing vessels such as oil tankers and aircraft carrier, and are carried by mobile firefighting vehicles including aircraft rescue firefighting trucks. A common component of AFFF-based fire suppression sprinkler systems has historically been per- and polyfluorinated alkyl substances (PFAS), but such systems have recently been the subject of regulations requiring their replacement owing to the toxicity of PFAS. As such, it is contemplated that decontamination of contaminated surfaces within a fire suppression sprinkler system may be accomplished via the presently disclosed cleaning in place methods in order to reduce the PFAS concentration to meet regulatory standards.

In such an exemplary method, is contemplated that an aqueous suspension may be provided which comprises 4,000 mg/L of colloidal activated carbon stabilized with 400 mg/L of carboxymethylcellulose. The suspension may be introduced into and flowed through the fire suppression sprinkler systems and maintained within the system such that the colloidal activated carbon comes into close contact with the areas in the system which may be contaminated with PFAS, resulting in the PFAS being drawn out and scoured from the contaminated surfaces, resulting in decontamination of those surfaces to the part-per-trillion (ppt) levels required by regulation of these compounds. The suspension may then be purged from the sprinkler system. As such, it may be seen that the sprinkler system may be cleaned-in-place, without requiring the system to be disassembled or otherwise transported to a different location for cleaning. In this way, it may be seen that use of the described suspension may serve to achieve cleaning in place in a far more efficient fashion than would be realized via purging the system using, for example, water alone, and relative to such purging with water alone, may result in a decrease of the amount of water required to achieve the desired level of contaminant reduction by up to 90%, which may be seen to result in substantial environmental benefits and cost savings, especially given the water used will likely not be readily reusable for other purposes.

It may however also be seen that any type of suspension in which the solid-phase particles is at least partially operative to at least partially decontaminate the at least one contaminated surface, without departing from the scope and spirit of the invention. Among other solid-phase materials, it is contemplated that the solid-phase particles utilized in the presently disclosed methods may be selected from: activated carbon, zeolites, alumina, apatite, iron oxides, iron oxyhydroxides, silica, silicates, titanium oxides, or combinations thereof. It may be seen that the particular selection of the solid-phase particle(s) included within the suspension may be tailored to more generally decontaminate a variety of pollutants, or may be specifically chosen to specifically decontaminate a particular pollutant, or to avoid an undesired reaction with a pollutant or other substance within or forming the mechanical system. Likewise, it may be seen that the particular selection of the other components of the suspension may also be tailored to assist in generally decontaminate a variety of pollutants, or may be specifically chosen to specifically decontaminate a particular pollutant, or to avoid an undesired reaction with a pollutant or other substance within or forming the mechanical system. For example, it may be seen that activated carbon might be useful as a more general decontaminant, while a substance which may create a reducing environment such as an iron oxide might be more suitable for use in decontaminating substances which may be prone to reductive decontamination, such as halogenated organic compounds. Likewise, it may be desirable for the suspension to be an aqueous suspension, or a non-aqueous suspension, according to the particular needs and economies involved in the particular application for which the presently disclosed cleaning-in-place methodology is to be applied. In particular, it may be seen that the specifics of the particular composition of the suspension are essentially infinitely variable, as will be further described, and that that such variation is specifically envisioned as being within the scope and spirit of the present disclosure, and is not to be interpreted as departing from the present disclosure.

In particular, it is contemplated that one way in which the particulars of the suspension may be varied to meet the needs of the presently disclosed methods may be to vary the amount of solid-phase particles included within the suspension. It is contemplated that in the exemplary embodiments, such solid-phase particles may be included within the suspension in any amount from 0.0001% to 70% by weight. However, to the extent that the solid-phase particles within the suspension are at least partially operative to at least partially decontaminate the at least one contaminated surface within the mechanical system, such boundaries are not to be interpreted as imposing a limit on the scope of the suspensions which may be used according to the presently described methods, and the amounts included may indeed be more than 70% by weight or less than 0.0001% by weight.

It is also contemplated that another important way in which the particulars of the suspension may be varied to meet the needs of the presently disclosed methods may be to vary the particle size distribution of the solid-phase particles within the suspension. Particle size distributions are commonly measured via particle size analysis, an analytical technique in which the distribution of sizes of a solid or liquid particulate material is measured. Techniques for particle size analysis may include sieve analysis, direct optical imaging, and laser diffraction. Data from sieve analysis, the oldest of these techniques, is typically presented in the form of an S-curve of cumulative mass retained on each sieve versus the sieve mesh size.

The most commonly used metric when describing a particle size distribution are D-values. D-values can be thought of as the cutoff point for the diameter that divides the sample mass into a specified percentage when the particles are arranged on an ascending mass basis. Thus, the D10, D50, and D90 value are the intercept points on the S-curve for 10%, 50%, and 90% of the cumulative mass respectively. D10 is the diameter size at which 10% of the sample's mass are comprised of particles with a diameter less than this size, D50 is the diameter size at which 50% of the sample's mass are comprised of particles with a diameter less than this size, and D90 is the diameter size at which 90% of the sample's mass are comprised of particles with a diameter less than this size. Because D-values are well-established, more advanced methods of measuring particle size distribution than sieve analysis may also report in D-values.

According to exemplary embodiments of the present disclosure the solid-phase particles may have a D90 value of less than 50 microns, which means that 90% of the mass of the solid-phase particles is comprised of particles having a diameter (i.e., of the largest dimension) of less than 50 microns. According to one more particular exemplary embodiment, the solid-phase particles may have a D90 of less than 15 microns. Such boundaries, however, are not to be interpreted as imposing a limit on the scope of the suspensions which may be used according to the presently described methods, and the D90 values of the solid-phase particles may be greater than 50 microns as well.

The suspension may also comprise one ore more reagents in addition to the plurality of solid-phase particles which are further operative to at least partially decontaminate the contaminated surface. Such reagents may be, for example, the solvent itself in which the solid-phase particles are suspended, which in the exemplary embodiment may be water, or reagents which are not itself the primary solvent. For example, the solvent may include liquids in solution which may be operative to at least partially decontaminate the contaminated surface, any number of which may be discernable by one of ordinary skill, which may be more general to a number of contaminants or types of contaminants, or which may be specific to one or a few particular contaminants.

The suspension may also comprise one or more additives, including but not limited to sodium carboxymethyl cellulose, polyacrylic acid, sodium lignosulfonate, polydiallyldimethylammonium chloride, alkyl carboxylates, alkyl and aryl sulfates, alkyl polyethylene oxides, ethylene oxides. Such additives may be included for various purposes, such as better improving the dispersion of the solid-phase particles, or as a surfactant, or for other purposes which will be readily apparent to those of skill in the art as a consequence of the known properties of these additive materials.

The suspension may also comprise one or more amendments, including but not limited to a biocide, a bleaching agent, chlorine, chloramine, a polyelectrolyte, a chelating agent, a buffering agent, a rheology modifier, a thickening agent, a thinning agent, a polymer, an oxidizing agent, a reducing agent, a surfactant, a bacterium, and combinations thereof. Such amendments may be included for any number of various purposes, such as, for example and without limitation, increasing or reducing the viscosity of the suspension, or for assisting in the process of decontamination of certain contamination, such as by the action of a bacterium in pacifying a contaminant.

The herein described methods are contemplated to be suitable for decontaminating contaminated surfaces which may comprise a wide range of organic contaminants, such as hydrocarbons, halogenated hydrocarbons, pesticides, herbicides, energetic materials, micropollutants, and combinations thereof. In particular, it is specifically contemplated that one exemplary embodiment of the herein described methods may be particularly suitable for decontaminated a contaminated surface comprising a halogenated hydrocarbon selected from: per- and polyfluoroalkyl substances (PFAS), a chlorinated solvent, or combinations thereof. In addition, it is also contemplated that the herein described methods may be suitable for decontaminating contaminated surfaces which may comprise inorganic contaminants which may include, among other things, heavy metals, anions, cations, and combinations thereof. It is further contemplated that the herein described methods may be suitable for decontaminating contaminated surfaces which may comprise pathogenic contaminants which may include, among other things, a bacteria, a virus, a protozoa, algae, fungi, viroids, prions, spores, and combinations thereof. Likewise, it may be seen that the herein described methods may be applicable to decontaminate contaminated surfaces which may comprise combinations of organic, inorganic, and pathogenic contaminants.

The step of introducing the suspension into the mechanical system having at least one contaminated surface such that the suspension comes into contact with the at least one contaminated surface may be performed according to any known way in which a suspension may be introducing into a mechanical system. For example, but without limitation, the suspension may be poured via gravity into the system, induced to enter into the system via positive or negative pressure, or placed proximal to the system (for example, via submersion of the system in the suspension) and allowed to flow into the system. These, however, are only to be interpreted as exemplary, and do not provide limits on the possible variations in ways in which the suspension may be introduced into the mechanical system according to the presently disclosed methods, and the ways described herein should be interpreted to include presently known and future developed ways of introducing the suspension into the mechanical system having at least one contaminated surface such that the suspension comes into contact with the at least one contaminated surface.

It may also be seen that according to the herein disclosed methods, following the introduction of the suspension into the mechanical system such that the suspension comes into contact with the at least one contaminated surface, the suspension must be maintained in contact with at least one contaminated surface for a sufficient length of time to at least partially decontaminate the at least one contaminated surface. It may thus be appreciated that the ways in which the suspension is be maintained in contact with the at least one contaminated surface, and the conditions under which the suspension is be maintained in contact with the at least one contaminated surface, are subject to variation in order to meet the particular requirements of the mechanical system, the contaminated surface, and/or the targeted contaminants. These described ways are only to be interpreted as exemplary, and do not provide limits on the possible variations in ways in which the suspension may be maintained within the mechanical system according to the presently disclosed methods, and the ways described herein should be interpreted to include presently known and future developed ways of maintaining the suspension in contact with the at least one contaminated surface for a sufficient length of time to at least partially decontaminate the at least one contaminated surface. For example, it may be seen that according to one embodiment, it may be desirable to simply introduce the suspension into the mechanical system and to let the suspension remain within the mechanical system with zero flow until such time has passed as sufficient decontamination has been achieved. However, it may also be seen that such decontamination may also be achieved, and may possibly better be achieved via other methods, such as letting the volume of the suspension flow through the mechanical system in a single pass or a certain defined number of passes, or by continuously recirculating the suspension through the mechanical system at a particular flow rate. The variations of the herein described methods which these may provoke may thus be seen to be prone to optimization by those skilled in the art to meet the particular needs at hand, and thus cannot be particularly defined herein. However, it may be seen that those of skill in the art may, through experimentation and using the guidelines established herein, determine such optimal conditions.

Likewise, other parameters may be modified to assist in optimizing the step of maintaining the suspension in contact with at least one contaminated surface for a sufficient length of time to at least partially decontaminate the at least one contaminated surface, including the temperature and pressure of the suspension. For example, it may be seen that it may be desirable to introduce and maintain the suspension at a particular pressure in order to assist in the solid phase particles contacting the surface to be decontaminated. It may further be seen that such pressure may be varied as a part of the methodology, for example, by introducing the suspension at a particular pressure and then raising the pressure following introduction. Similarly, it may be seen that the temperature of the suspension may be another factor which may be controlled in order to result in better optimization of the decontamination process, and such controlling may include varying the temperature to be higher or lower, or both at different times, during the process following the introduction of the suspension into the mechanical system. Indeed, the variation which may be achieved via modification of these parameters, by themselves or in combination with any number of the other parameters described herein, or other parameters which would be apparent to one of ordinary skill in the art, are to be understood as essentially limitless, and as such, the resulting specific variations which may result from the application of the general principals of the methods described herein are to be understood as within the scope and spirit of the present disclosure.

Following the step of maintaining the suspension in contact with at least one contaminated surface for a sufficient length of time to at least partially decontaminate the at least one contaminated surface, the suspension may be purged from the system. This purging step may be achieved by any known way in which a suspension may be purged from a mechanical system, including, for example but without limitation, outflow from the system via gravity or hydraulic or pneumatic pressure, vaporization, destructive distillation, or other forms of purging readily apparent to those of skill in the art. It may further be appreciated that following the step purging the suspension from the mechanical system, further cleaning processes for at least partially decontaminating the at least one contaminated surface may be performed, which may include, for example, further application of the herein described methods, either using the same or a different formulation of suspension under either the same or different conditions or parameters, or entirely distinct methods of cleaning. In addition, or alternatively, such further cleaning processes for at least partially decontaminating the at least one contaminated surface may be performed prior to the herein described methods.

It is further contemplated that following the step of purging the suspension from the system, or contemporaneous therewith, the suspension may be filtered to at least partially isolate the solid-phase particulate from the remainder of the suspension via a filtration step. In this fashion, it may be seen that, for certain suspensions which may operate upon a surface to be decontaminated via the solid-phase particulate adsorbing the contaminants, it may be possible to regenerate or otherwise re-use the remainder of the suspension via safely discarding the isolated solid-phase particulate which contains the removed contaminants or any byproducts thereof, by unused solid-phase particulate to replace the quantity removed. Thus, it may be seen that the consumption of solvent or other components of the suspension during the process of cleaning-in-place may be reduced even further, and the environmental benefits of this approach may be readily appreciated. Such filtration may be achieved by, among other things, a membrane filtration system, filter press, or by other mechanical means of isolating solids from the suspension. The efficiency gains of this approach may also relate to the filtration process permitting the remainder of the solution following the at least partial isolation of the solid-phase particulate to be disposed of according to readily feasible methods, rather than requiring special methods of containment or disposal that would be necessary without a filtration step. Likewise, a filtration step of this type may result in the resulting volume which requires special methods of containment or disposal being correspondingly reduced. It is also contemplated that prior to any disposal of any portion following filtration may be performed after a testing step to determine the level of contamination and/or the effectiveness of the contaminant removal process.

The above description is given by way of example, and not limitation. Given the above disclosure, one skilled in the art could devise variations that are within the scope and spirit of the invention disclosed herein. Further, the various features of the embodiments disclosed herein can be used alone, or in varying combinations with each other and are not intended to be limited to the specific combination described herein. Thus, the scope of the claims is not to be limited by the illustrated embodiments.

What is claimed is:

1. A method of cleaning a contaminated surface comprising per- and polyfluoroalkyl substances (PFAS) within an aboveground fire suppression system, the method comprising the steps of:
   introducing a suspension into the aboveground fire suppression system having at least one contaminated surface comprising the PFAS such that the suspension comes into contact with the at least one contaminated surface, the suspension comprising a plurality of solid-phase particles;
   maintaining the suspension in contact with the at least one contaminated surface for a sufficient length of time to at least partially decontaminate the at least one contaminated surface via adsorption of at least some of the PFAS by the plurality of solid-phase particles, the suspension being allowed to remain in the aboveground fire suppression system with zero flow during said maintaining step; and
   purging the suspension from the aboveground fire suppression system;
   wherein the method results in a reduction of PFAS concentration in the aboveground fire suppression system to meet a regulatory standard.

2. A method of cleaning a contaminated surface comprising per- and polyfluoroalkyl substances (PFAS) within an aboveground fire suppression system, the method comprising the steps of:
   choosing a solid-phase particle to specifically decontaminate the PFAS of at least one contaminated surface of the fire suppression system contaminated surface by adsorption;
   providing a suspension comprising a plurality of the solid-phase particles;
   introducing the suspension into the aboveground fire suppression system having the at least one contaminated surface such that the suspension comes into contact with the at least one contaminated surface;
   maintaining the suspension in contact with the at least one contaminated surface for a sufficient length of time to at least partially decontaminate the at least one contaminated surface via adsorption of at least some of the PFAS by the plurality of the solid-phase particles; and
   purging the suspension from the aboveground fire suppression system;
   wherein the method results in a reduction of PFAS concentration in the aboveground fire suppression system to meet a regulatory standard.

3. The method of claim 2, wherein the solid-phase particles are present within the suspension in an amount from 0.0001% to 70% by weight.

4. The method of claim 2, wherein during the step of maintaining the suspension in contact with the at least one contaminated surface, the suspension is maintained at a predefined temperature.

5. The method of claim 2, wherein during the step of maintaining the suspension in contact with the at least one contaminated surface, the temperature of the suspension is varied.

6. The method of claim 2, wherein during the step of maintaining the suspension in contact with the at least one contaminated surface, the suspension is maintained at a predefined pressure.

7. The method of claim 2, wherein during the step of maintaining the suspension in contact with the at least one contaminated surface, the pressure of the suspension is varied.

8. The method of claim 2, wherein the suspension further comprises one or more reagents in addition to the plurality of solid-phase particles, the one or more reagents being further operative to at least partially decontaminate the contaminated surface.

9. The method of claim 2, wherein the plurality of solid-phase particles comprise: activated carbon, zeolites, alumina, apatite, iron oxides, iron oxyhydroxides, silica, silicates, titanium oxides, or combinations thereof.

10. The method of claim 2, wherein the contaminated surface further comprises inorganic contaminants selected from: heavy metals, anions, cations, and combinations thereof.

11. The method of claim 2, wherein the suspension further comprises one or more additives selected from: sodium carboxymethyl cellulose, polyacrylic acid, sodium lignosulfonate, polydiallyldimethylammonium chloride, alkyl carboxylates, alkyl and aryl sulfates, alkyl polyethylene oxides, ethylene oxides, and combinations thereof.

12. The method of claim 2, wherein the suspension further comprises one or more amendments selected from: a biocide, a bleaching agent, chlorine, chloramine, a polyelectrolyte, a chelating agent, a buffering agent, a rheology modifier, a thickening agent, a thinning agent, a polymer, an oxidizing agent, a reducing agent, a surfactant, a bacterium, and combinations thereof.

13. The method of claim 2, wherein said fire suppression system is an aqueous film-forming foam-based fire suppression system.

14. The method of claim 2, wherein the aboveground fire suppression system further comprises machineries, pipeworks, vessels or combinations thereof; and wherein the fire suppression system is found in a firefighting truck, an aircraft hanger, a refinery, a seagoing vessel, or combinations thereof.

15. The method of claim 2, wherein in the suspension, the solid-phase particles have a particle size distribution D90 value of less than 50 microns.

16. The method of claim 15, wherein in the suspension, the solid-phase particles have a particle size distribution D90 value of less than 15 microns.

17. The method of claim 2, where following the step of purging the suspension from the fire suppression system, at least a portion of the plurality of solid-phase particles are isolated from the suspension via a filtration step.

18. The method of claim 17, where following the step of isolating said portion of the plurality of solid-phase particles from the suspension via filtration, said suspension is re-used in the step of introducing a suspension into an aboveground fire suppression system.

19. The method of claim 2, wherein the contaminated surface further comprises organic contaminants selected from: hydrocarbons, halogenated hydrocarbons, pesticides, herbicides, energetic materials, micropollutants, and combinations thereof.

20. The method of claim 19, wherein the contaminated surface further comprises a chlorinated solvent.

* * * * *